United States Patent [19]

Kanemura et al.

[11] Patent Number: 5,191,055
[45] Date of Patent: Mar. 2, 1993

[54] MERCAPTO COMPOUND, A HIGH REFRACTIVE INDEX RESIN AND LENS AND A PROCESS FOR PREPARING THEM

[75] Inventors: Yoshinobu Kanemura; Katsuyoshi Sasagawa; Masao Imai, all of Yokohama; Toshiyuki Suzuki, Kamakura, all of Japan

[73] Assignee: Mitsui Toatsu Chemicals, Inc., Tokyo, Japan

[21] Appl. No.: 885,251

[22] Filed: May 20, 1992

Related U.S. Application Data

[60] Continuation of Ser. No. 794,897, Nov. 20, 1991, abandoned, which is a division of Ser. No. 399,990, Aug. 29, 1989, Pat. No. 5,087,758.

[30] Foreign Application Priority Data

Dec. 22, 1988 [JP] Japan .................... 63-321928

[51] Int. Cl.$^5$ .................... C08G 18/32; C08G 18/48
[52] U.S. Cl. .................... 528/77; 528/76; 528/374; 528/378; 568/57; 568/39; 568/45; 568/50; 568/62
[58] Field of Search ............ 528/77, 374, 378, 76; 568/57, 39, 45, 50, 62

[56] References Cited

U.S. PATENT DOCUMENTS

| | | | |
|---|---|---|---|
| 4,443,588 | 4/1984 | Fukuda et al. | 528/75 |
| 4,680,369 | 7/1987 | Kajimoto et al. | 528/76 |
| 4,689,387 | 8/1987 | Kajimoto et al. | 528/76 |
| 4,775,733 | 10/1988 | Kanemura et al. | 528/67 |
| 4,780,522 | 10/1988 | Kajimoto et al. | 528/76 |
| 4,791,185 | 12/1988 | Kanemura et al. | 528/73 |
| 4,820,789 | 4/1989 | Gonzalez et al. | 528/55 |
| 4,929,707 | 5/1990 | Nagata et al. | 528/76 |
| 5,059,673 | 10/1991 | Kanemura et al. | 528/67 |

FOREIGN PATENT DOCUMENTS

| | | |
|---|---|---|
| 57-136601 | 8/1982 | Japan . |
| 58-164615 | 9/1983 | Japan . |
| 60-194401 | 10/1985 | Japan . |
| 62-267316 | 11/1987 | Japan . |

OTHER PUBLICATIONS

Chemical Abstracts, vol. 104, No. 7, Feb. 1986, p. 488, Abstract No. 50541p.
Chemical Abstracts, vol. 104, No. 15, Apr. 1986, p. 663, Abstract No. 129491f.

*Primary Examiner*—John Kight, III
*Assistant Examiner*—Duc Truong
*Attorney, Agent, or Firm*—Burns, Doane, Swecker & Mathis

[57] ABSTRACT

The present invention relates to a mercapto compound, a process for preparing the mercapto compound, a process for preparing a polythiourethane base resin containing the mercapto compound, and a process for preparing plastic lenses containing the resin.

9 Claims, No Drawings

MERCAPTO COMPOUND, A HIGH REFRACTIVE INDEX RESIN AND LENS AND A PROCESS FOR PREPARING THEM

This application is a continuation of application Ser. No. 07/794,897, filed Nov. 20, 1991, now abandoned, which is a divisional of the application Ser. No. 07/399,990, filed Aug. 29, 1989, now U.S. Pat. No. 5,087,758.

BACKGROUND OF THE INVENTION

The present invention relates to a mercapto compound, a process for preparing a mercapto compound, a process for preparing a polythiourethane base resin containing the mercapto compound, and a process for preparing plastic lenses containing the resin. The mercapto compound of the invention is useful as a crosslinking agent, a hardener for epoxy resin, a vulcanizing agent, a polymerization modifier, a raw material of plastic resin, an antioxidant, a metal complex forming agent, a biochemical agent and a lubricating oil additive.

DESCRIPTION OF THE PRIOR ART

A resin presently widely used for plastic lenses is a radical polymerization product of diet-hyleneglycol-bis(allylcarbonate) (hereinafter abbreviated as DAC). The resin has good impact resistance, is lightweight, has prominent dye affinity, good machinability, and cutting and polishing ability. However, lenses prepared from the resin have a lower refractive index ($n_D = 1.50$) than inorganic lenses ($n_D = 1.52$) have. In order to obtain equivalent optical properties as glass lenses, the center thickness, peripheral thickness and curvature of the lens must be increased, which results in a thick lens.

Other resins useful in preparing plastic lenses having good refractive indexes are polyurethane base resins obtained by reacting isocyanate compounds with hydroxyl compounds such as diethylene glycol (Japanese Patent Laid-Open No. 136601/1982, U.S. Pat. No. 4,443,588), with halogen containing hydroxyl compounds such as tetrabromobisphenol-A (Japanese Patent Laid Open No. 164615/1983), with sulfur containing hydroxyl compounds (Japanese Patent Laid-Open Nos. 194401/1985 and 217229/1985, U.S. Pat. Nos. 4,680,369 and 4,780,522), and with polythiol compounds (Japanese Patent Laid-Open Nos. 199016/1985, 267316/1987, and 46213/1988, U.S. Pat. No. 4,689,387). However, the lenses prepared from these resins exhibit unsatisfactory refractive indexes, although the indexes of these lenses are better than those of lenses prepared from DAC. Further, since these resins are prepared from compounds containing many halogen atoms or aromatic rings to improve the refractive index, lenses containing these resins have disadvantages such as large dispersion of refractive index, poor weatherability and high specific gravity.

Since the indexes of the above lenses are unsatisfactory, and problems in heat resistance during processing such as dyeing, coating and the like exist, and since sulfurous odors of sulfur compounds employed in the prior art may affect the operators' health at the time of preparing lenses, further improved resin compositions are desired.

SUMMARY OF THE INVENTION

The present invention overcomes the problems and disadvantages of prior art resins by providing a novel mercapto compound, a polythiourethane resin containing the mercapto compound, plastic lenses comprising the resin, and processes for producing them.

An object of the invention is to provide a novel mercapto compound having insensible sulfurous odor.

Another object of the invention is to provide a process to prepare the mercapto compound reacting a glycerin derivative or a epihalohydrin with 2-mercapto ethanol to get an triol, and reacting the alcohol with a thiourea to form the mercapto compound.

Another object of this invention is to provide a colorless and transparent polythiourethane base resin having a high refractive index and low dispersion of refractive index which is suitable for use in producing a lens that is lightweight, excellent in weatherability and exhibits high impact and heat resistance.

A further object of the invention is to provide a polythiourethane base lens having high accuracy in the profile of surface and excellent optical properties.

Additional objects and advantages of the invention will be set forth in part in the description which follows, and in part will be obvious from the description, or may be learned by practice of the invention. The objects and advantages of the invention will be realized and attained by means of the instrumentalities and combinations, particularly pointed out in the appended claims.

To achieve the objects and in accordance with the purpose of the invention, as embodied and broadly described herein, the invention provides a mercapto compound of the formula (I) and a process for preparing same

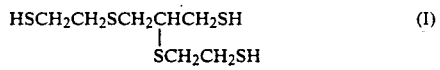

comprising reacting a thio compound with a triol compound of the formula (II) or (III)

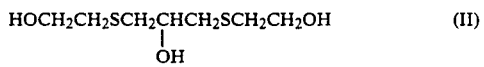

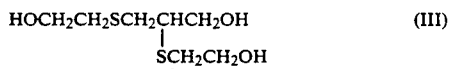

The invention also provides for a polythiourethane base resin comprising reacting the mercapto compound of the formula (I) with one or more ester compounds selected from the group consisting of polyisocyanate compounds, polyisothiocyanate compounds and isothiocyanate compounds having isocyanato groups and a process for producing the resin.

The present invention further provides a lens comprising the resin and a process for producing the lens containing the resin of the invention comprising forming a mixture of the mercapto compound of the formula (I) and one or more ester compounds selected from the group consisting of polyisocyanate compounds, polyisothiocyanate compounds and isothiocyanate compounds having isocyanate groups, pouring the mixture into a mold and polymerizing the mixture to form a lens.

DESCRIPTION OF THE PREFERRED EMBODIMENTS

Reference will now be made in detail to the present preferred embodiments of the invention.

The mercapto compound of the formula (I) can be prepared by reacting a thio compound with the triol compound of the formula (II) or (III) to substitute three hydroxy groups of the triol compound for three mercapto groups. The reaction can be carried out by known hydrolysing methods such as alkali hydrolysis after reacting the triol compound with thiourea in mineral acid. In these circumstances, rearrangement between —OH and —SCH$_2$CH$_2$OH of formula (II) takes place to form the mercapto compound represented by formula (I).

The triol compound of the formula (II)

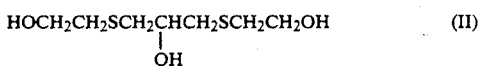
(II)

can be prepared by reacting a glycerol derivative or epihalohydrin with 2-mercaptoethanol.

Further, the triol compound of the formula (III) can be prepared by a reaction 2-mercapto ethanol with a glycerine derivative such as 2,3-dibromo-1-propanol.

For example, the mercapto compound of formula (I) can be prepared by adding epichlorohydrin dropwise into an aqueous solution or a lower alcohol, e.g. methanol or ethanol, solution containing 2-mercaptoethanol and a base. In this instance, a reaction temperature between 0° C. to 120° C. is preferable.

2-Mercaptoethanol is needed more than 2 molar equivalent for epichlorohydrin, and preferably in a range of 2 to 3.

Exemplary suitable base includes a metal hydroxide such as sodium or potassium hydroxide, a metal carbonate such as sodium or potassium carbonate and a tertiary amine such as triethylamine or tributyl amine. Sodium hydroxide is most preferably used because of its inexpensiveness and enough reactivity in molar amounts of more than moles of epichlorohydrin but of less than moles of 2-mercaptoethanol.

To avoid coloring on reactant, the above synthesis is preferably carried out by two steps. For example, at first epichlorohydrin is added dropwise into an aqueous or a lower alcoholic such as of methanol or ethanol solution which contains one to three molar equivalent of 2-mercaptoethanol for epichlorohydrin and catalytic amount, preferably 0.001 to 0.1 molar equivalent, of the base to get a diol compound of formula (IV).

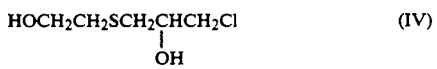
(IV)

and then 2-mercaptoethanol and the base added to the resulted reactant, respectively to reach two to three and one to two molar equivalent including their respective amounts used at first step to get the triol of formula (II) in second step.

Reacting temperature at first step when strong base is used, is preferable at 0° to 50° C. When the temperature exceeds 50° C., catalytical base acts to form the triol from the diol, and reduces the yield of the diol. In case that of tertiary amine is used at first step, no such a problem arise at a temperature of 50° to 120° C.

Resulted triol compound of formula (II) is reacted with at least three, preferably three to six, molar equivalent of thiourea, in an mineral acid aqueous solution containing at least three, preferably three to twelve, molar equivalent at a temperature of room to refluxing.

Exemplary mineral acid used in above case includes hydrochloric acid, hydrobromic acid, hydroiodic acid, sulfuric acid and phosphoric acid.

Hydrochloric acid is preferable because of enough reaction velocity and avoiding coloring on product.

Following hydrolysis is carried out by bringing the above resulted reactant to alkali with a metal hydroxide, such as sodium hydroxide, potassium hydroxide, ammonia or a amine, such as triethyl amine, in amount of at least three, preferably three to twelve, molar equivalent at a temperature of room to refluxing. When adding those alkali to resulted reactant, a temperature of 0° to 50° C. is preferable not to cause coloring.

The thus produced mercapto compound of formula (I) is purified after extracting by an organic solvent such as toluene by common methods such as washing by acid and water, condensation or filtration, and further distillation is also applicable.

Although the above all steps may practise in air, all steps are preferably practised under nitrogen atmosphere.

The polythiourethane base resin of the present invention is prepared by reacting the mercapto compound of the formula (I) with one or more ester compounds selected from the group consisting of polyisocyanate compounds, polyisothiocyante compounds and isothiocyanate compounds having isocyanato groups.

Exemplary suitable compounds useful as the polyisocyanate compound in the process of the invention include aliphatic polyisocyanate compounds such as ethylene diisocyanate, trimethylene diisocyanate, tetramethylene diisocyanate, hexamethylene diisocyanate, octamethylene diisocyanate, nonamethylene diisocyanate, 2,2'-dimethylpentane diisocyanate, 2,2,4-trimethylhexane diisocyanate, decamethylene diisocyanate, butene diisocyanate, 1,3-butadiene-1,4-diisocyanate, 2,4,4-trimethylhexamethylene diisocyanate, 1,6,11-undecane triisocyanate, 1,3,6-hexamethylene triisocyanate, 1,8-diisocyanato-4-isocyanatomethyloctane, 2,5,7-trimethyl-1,8-diisocyanato-5-isocyanatomethyloctane, bis(isocyanatoethyl)carbonate, bis(isocyanatoethyl)ether, 1,4-butyleneglycol dipropylether-ω,ω'-diisocyanate, lysine diisocyanatomethyl ester, lysine triisocyanate, 2-isocyanatoethyl-2,6-diisocyanato hexanoate, 2-isocyanatopropyl-2,6-diisocyanato hexanoate, xylylene diisocyanate, bis(isocyanatoethyl)benzene, bis(isocyanatopropyl)benzene, α,α,α',α'-tetramethylxylylene diisocyanate, bis(isocyanatobutyl)benzene, bis(isocyanatomethyl)naphthalene, bis(isocyanatomethyl)diphenyl ether, bis(isocyanatoethyl)phthalate, mesitylylene triisocyanate and 2,6-di(isocyanatomethyl)furan; alicyclic polyisocyanates such as isophorone diisocyanate, bis(isocyanatomethyl)cyclohexane, dicyclohexylmethane diisocyanate, cyclohexane diisocyanate,methylcyclohexane diisocyanate, dicyclohexyldimethylmethane diisocyanate, 2,2'-dimethyldicyclohexylmethane diisocyanate, bis(4-isocyanato-n-butylidene)-pentaerythritol, dimer acid diisocyanate, 2-isocyanatomethyl-3-(3-isocyanatopropyl)-5-isocyanatomethyl-bicyclo-(2,2,1)-heptane, 2-isocyanatomethyl-3-(3-isocyanatopropyl)-6-isocyanatomethyl-bicyclo(2,2,1)-heptane, 2-isocyanatomethyl-2-(3-isocyanatopropyl)-5- isocyanatomethylbicyclo-(2,2,1)-heptane, 2-isocyanatomethyl-2-(3-isocyanatopropyl)-6-isocyanatomethyl-bicyclo(2,2,1)-heptane, 2-isocyanatomethyl-3-(3-isocyanatopropyl)-5-(2-isocyanatoethyl)-bicyclo-(2,2,1)-heptane, 2-isocyanatomethyl-3-(3-isocyanatopropyl)-6-(2-isocyanatoethyl)-bicyclo-(2,2,1)-heptane, 2-isocyanatomethyl-2-(3-isocyanatopropyl)-5-(2-isocyanatoethyl)-bicyclo-(2,2,1)-heptane and 2-isocyanatomethyl-2-(3-isocyanatopropyl)-6-(2-isocyanatoethyl)-bicyclo-(2,2,1)-heptane; and aromatic polyisocyanates such as phenylene diisocyanate, tolylene diisocyanate, ethylphenylene diisocyanate, isopropylphenylene diisocyanate, dimethylphenylene diisocyanate, diethylphenylene diisocyanate, diisopropylphenylene diisocyanate, trimethylbenzene triisocyanate, benzene triisocyanate, naphthalene diisocyanate, methylnaphthalene diisocyanate, biphenyl diisocyanate, tolidine diisocyanate, 4,4'-diphenylmethane diisocyanate, 3,3'-dimethyldiphenylmethane-4,4'-diisocyanate, bibenzyl-4,4'-diisocyanate, bis(isocyanatophenyl)-ethylene, 3,3'-dimethoxybiphenyl-4,4'-diisocyanate, triphenylmethane triisocyanate, polymeric MDI, naphthalene triisocyanate, diphenylmethane-2,4,4'-triisocyanate, 3-methyldiphenylmethane-4,6,4'-triisocyanate, 4-methyl-diphenylmethane-3,5,2',4',6'-pentaisocyanate, phenylisocyanatomethyl isocyanate, phenylisocyanatoethyl isocyanate, tetrahydronaphthylene diisocyanate, hexahydrobenene diisocyanate, hexahydrodiphenylmethane-4,4'-diisocyanate, diphenyl ether diisocyanate, ethylene glycol diphenyl ether diisocyanate, 1,3-propylene glycol diphenyl ether diisocyanate, benzophenone diisocyanate, diethylene glycol diphenyl ether diisocyanate, dibenzofuran diisocyanate, carbazole diisocyanate, ethylcarbazole diisocyanate and dichlorocarbazole diisocyanate; sulfur containing aliphatic polyisocyanates such as thiodiethyl diisocyanate, thiodipropyl diisocyanate, thiodihexyl diisocyanate, dimethyl sulfone diisocyanate, dithiodimethyl diisocyanate, dithiodiethyl diisocyanate, and dithiodipropyl diisocyanate; sulfide linkage containing aromatic polyisocyanates such as diphenylsulfide-2,4'-diisocyanate, diphenylsulfide-4,4'-diisocyanate, 3,3'-dimethoxy-4,4'-diisocyanatodibenzyl thioether, bis(4-isocyanatomethylphenyl)sulfide, and 4,4-methoxyphenylthioethyleneglycol-3,3'-diisocyanate; disulfide linkage containing aromatic polyisocyanates such as diphenyldisulfide-4,4'-diisocyanate, 2,2'-dimethyldiphenyldisulfide-5,5'-diisocyanate, 3,3'-dimethyldiphenyldisulfide-5,5'-diisocyanate, 3,3'-dimethyldiphenyldisulfide-6,6'-diisocyanate, 4,4'-dimethyldiphenyldisulfide-5,5'-diisocyanate, 3,3'-dimethoxydiphenyldisulfide-4,4'-diisocyanate, and 4,4'-dimethoxydiphenyldisulfide-3,3'-diisocyanate; sulfone linkage containing aromatic polyisocyanates such as diphenylsulfone-4,4'-diisocyanate, diphenylsulfone-3,3'-diisocyanate, benzidinesulfone-4,4'-diisocyanate, diphenylmethanesulfone-4,4'-diisocyanate, 4-methyldiphenylsulfone-2,4'-diisocyanate, 4,4'-dimethoxydiphenylsulfone-3,3'-diisocyanate, 3,3'-dimethoxy-4,4'-diisocyanatodibenzyl sulfone, 4,4'-dimethyldiphenylsulfone-3,3'-diisocyanate, 4,4'-di-tert-butyldiphenylsulfone-3,3'-diisocyanate, 4,4'-methoxyphenylethylenedisulfone-3,3'-diisocyanate, and 4,4'-dichlorodiphenylsulfone-3,3'-diisocyanate; sulfonic acid ester linkage containing aromatic polyisocyanates such as 4-methyl-3-isocyanatophenylsulfonyl-4'-isocyanatophenol ester and 4-methoxy-3-isocyanatophenylsulfonyl-4'-isocyanatophenol ester; sulfonamide linkage containing aromatic polyisocyanates such as 4-methyl-3-isocyanatophenylsulfonylanilide-3'-methyl-4'-isocyanate, diphenylsulfonylethylenediamine-4,4'-diisocyanate, 4,4'-methoxyphenylsulfonylethylene-diamine-3,3'-diisocyanate, and 4-methyl-3-isocyanatophenylsulfonylanilide-4-methyl-3'-isocyanate;sulfur containing heterocyclic compounds such as thiophene-2,5-diisocyanate; and 1,4-dithian-2,5-diisocyanate.

In addition, halogen-substituted compounds such as chlorine-substituted and bromine-substituted compounds, alkyl-substituted compounds, alkoxy-substituted compounds, nitro-substituted compounds, polyvalent alcohol-modified prepolymer type compounds, carbodiimido-modified compounds, urea-modified compounds, biuret-modified compounds of the above polyisocyanate compounds, and products of dimerization and trimerization reactions of these polyisocyanate compounds may be employed.

Exemplary suitable polyisothiocyanate compounds useful in the process of invention include such compounds having two or more functional isothiocyanato groups in the molecule, and may also contain a sulfur atom, such as aliphatic polyisothiocyanate compounds, for example, 1,2-diisothiocyanatoethane, 1,3-diisothiocyanatopropane, 1,4-diisothiocyanatobutane, 1,6-diisothiocyanatohexane, p-phenylenediisopropylidenediisothiocyanate; alicyclic polyisothiocyanate compounds such as cyclohexanediisothiocyanate; aromatic polyisothiocyanates such as 1,2-diisothiocyanatobenzene, 1,3-diisothiocyanatobenzene, 1,4-diisothiocyanatobenzene, 2,4-diisothiocyanatotoluene, 2,5-diisothiocyanato-m-xylene, 4,4'-diisothiocyanato-1,1'-biphenyl, 1,1'-methylenebis(4-isothiocyanatophenyl), 1,1'-methylenebis(4-isothiocyanato-2-methylphenyl), 1,1'-methylenebis(4-isothiocyanato-3-methylphenyl), 1,1'-(1,2-ethanediyl)bis(4-isothiocyanatophenyl), 4,4'-diisothiocyanatobenzophenone, 4,4'-diisothiocyanato-3,3'-dimethylbenzophenone, benzanilide-3,4'-diisothiocyanate, diphenylether-4,4'-diisothiocyanate, diphenylamine-4,4'-diisothiocyanate; isothiocyanates containing a heterocyclic ring such as 2,4,6-triisothiocyanato-1,3,5-triazine; carbonylisothiocyanates such as hexanedioyldiisothiocyanate, nonanedioyldithiocyanate, carbonic diisothiocyanate, 1,3-benzenedicarbonyl diisothiocyanate, 1,4-benzenedicarbonyldiisothiocyanate, (2,4'-bipyridyl)-4,4'-dicarbonyldiisothiocyanate.

Exemplary compounds suitable for use as a polyisothiocyanate compound containing at least two isothiocyanato groups and at least one sulfuratom in the process of the invention include sulfur-containing aliphatic isothiocyanate compounds such as thiobis(3-isothiocyanatopropane), thiobis(2-isothiocyanatoethane), dithiobis(2-isothiocyanatoethane); sulfur-containing aromatic isothiocyanate such as 1-isothiocyanato-4-[(2-isothiocyanato)sulfonyl]benzene, thiobis(4-isothiocyanatophenyl), sulfonylbis(4-isothiocyanatophenyl), sulfinylbis(4-isothiocyanatophenyl), 4-isothiocyanato-1-[(4-isothiocyanatophenyl)sulfonyl]-2-methoxybenzene, 4-methyl-3-isothiocyanatobenzenesulfonyl-4'-isothiocyanatophenylester, 4-methyl-3-isothiocyanatobenzenesulfonylanilide-3'-methyl-4'-isothiocyanate; sulfur containing heterocyclic compounds such as thiophenone-2,5-diisothiocyanate and 1,4-dithian-2,5-diisothiocyanate.

In addition, halogen-substituted compounds such as chlorine-substituted and bromine-substituted compounds, alkyl-substituted compounds, alkoxy-substituted compounds, nitro-substituted compounds, polyvalent alcohol-modified prepolymer type compounds, carbodiimido-modified compounds, urea-modified compounds, biuret-modified compounds of the above polyisothiocyanate compounds, and products of dimerization and trimeriation reactions of these polysiothiocyanate compounds may be employed.

Exemplary suitable compounds useful as isothiocyanate compounds having isocyanato groups in the process of the invention include aliphatic or alicyclic compounds such as 1-isocyanato-3-isothiocyanatopropane, 1-isocyanato-5-isothiocyanatopentane, 1-isocyanato-6-isothiocyanatohexane, isothiocyanatocarbonylisocyanate, 1-isocyanato-4-isothiocyanatocyclohexane; aromatic compounds such as 1-isocyanato-4-isothiocyanato benzene and 4-methyl-3-isocyanato-1-isothiocyanato benzene; heterocyclic compounds such as 2-isocyanato-4,6-diisothiocyanato-1,3,5-triazine; compounds having a sulfur atom and an additional isothiocyanato group such as 4-isocyanato-4'-isothiocyanato diphenyl sulfide and isocyanato-2'-isothiocyanatodiethyldisulfide.

Halogen-substituted compounds such as chlorine substituted and bromine-substituted compounds, alkyl-substituted compounds, and alkoxy-substituted compounds, nitro-substituted compounds, polyvalent alcohol-modified prepolymer type compounds, carbodiimido-modified compounds, urea-modified compounds, biuret-modified compounds of the above isothiocyanate compounds, and products of dimerization and trimerization reactions of these isothiocyanate compounds may also be employed.

The ester compounds may be used alone or i combination as a mixture. The proportion of the ester compounds to the mercapto compound of the formula (I) is a mole ratio of from about 0.5 to about 3.0 moles of functional (NCO+NCS) group per mole of functional mercapto group, preferably from about 0.5 to about 1.5 moles of functional (NCO+NCS) group per mole of functional mercapto group.

In the plastic lens of the present invention, an S-alkyl thiocarbamic acid ester resin or a dithiourethane resin may be employed as a raw material, and therefore in the lens an S-alkyl thiocarbamic acid ester bond is present between an isocyanato group and a mercapto group, or a dithiourethane bond is present between an isothiocyanato group and a mercapto group. However, the plastic lens of the invention may also contain an allophanate bond, a urea bond, or a biuret bond. For example, it may be desirable to further react the isocyanato group with the S-alkyl thiocarbamic acid ester bond, or to react the isothiocyanato group with the dithiourethane bond to increase the cross-link density. Such a reaction may be carried out at a temperature of at least 100° C. and the isocyanato or isothiocyanato component should be used in an excess amount. Alternatively, an amine compound or the like may also be used to produce a urea bond or a biuret bond. When the isocyanate compound and/or isothiocyanate compound is reacted with a compound other than the mercapto compound, attention should be paid to coloring.

Various additives may be added to the above raw materials. Exemplary suitable additives include an internal mold releasing agent, a chain extender, a cross-linking agent, a light stabilizer, an ultraviolet absorber, an anti-oxidant, an oil-soluble dye and a filler.

The reaction rate may be adjusted to a desired level by adding a known reaction catalyst useful in the manufacture of a polyurethane.

The plastic lens of the present invention can be prepared by cast polymerization. A mercapto compound of the formula (I) and one or more ester compounds are mixed to form a mixture. The mixture is then poured into a mold, degasified if necessary, followed by polymerization. To facilitate releasing the lens from a mold after polymerization, the mold can be treated with a known release method.

The resin of the present invention does not give workers an unpleasant feeling from sulfurous odors of its monomers during treating, and during and after processing.

The resin has a very low dispersion property, a high refractive index, is excellent in heat resistance and is colorless and transparent. The resin is also lightweight, has excellent weatherability and impact resistance.

The resin is suitable for use as optical element material such as eyeglass lenses and camera lenses, and for glazing materials, paint and bonding materials.

Moreover, the plastic lenses of the present invention can be subjected to physical and chemical treatment such as surface abrasion treatment, antistatic treatment, hard coat treatment, non-reflective coat treatment, coloring treatment and dimming treatment for prevention of reflection, enhancement of hardness, improvement of abrasion resistance and chemical resistance, prevention of turbidity, supply of fashionability, and the like.

The invention will be further described and clarified by the following examples and comparative examples which are intended to be purely exemplary of the invention.

The performance tests of the resins and lenses, specifically the tests of refractive index, Abbe's number, weatherability, appearance and odor were carried out by the following procedure:

Refractive index and Abbe's number:
Measured at 20° C. with a Pulfrich refractometer.
Weatherability:
A lens resin was set in a weatherometer equipped with a sunshine carbon arc lamp. The lens was taken out after 20 hours and its hue was compared with that of a lens resin before the test. Evaluation was classified into no change (0), slight yellowing (Δ), and yellowing (X).
Appearance:
Evaluation was conducted by visual observation.
Odor:
Evaluation has classified into little smelling (0), slight smelling (Δ) and strong smelling (X) of sulfurous odor upon mixing the monomer.
Heat resistance:
Test pieces were separately heated at a rate of 2.5° C./min under a load of 5 g by means of a "Thermomechanical Analyzer" (manufactured by perkin-Elmer Company, U.S.A.) to measure their heat-distortion starting temperatures.

EXAMPLE 1

Synthesis of the mercapto compound of formula (I):
53.2 g (0.681 mol) of 2-mercapto ethanol and 271.2 g (0.680 mol) of sodium hydroxide were dissolved in 200 ml of ethanol and homogenized. 30.0 g (0.324 mol) of epichlorohydrin were added dropwise to the ethanol solution while maintaining an inner temperature of 15° C.

The mixture was heated to 50° C. and stirred for one hour. The reaction mixture was cooled at room temperature and 40.5 g (0.399 mol) of hydrochloric acid (36%) were added to form a precipitate. The salt precipitated was separated by filtration with suction. The filtrate was concentrated under reduced pressure and 70.6 g of 1,3-bis(2-hydroxyethylthio)-2-propanol (formula (II) compound) were obtained as a colorless and viscous liquid.

The produce was dissolved in 203 g (2.00 mol) of hydrochloric aqueous solution (36%) and 92.6 g (1.22 mol) of thiourea were added to the solution. The solution was heated and stirred for six hours at 110° C. The solution was cooled to room temperature, and 195 g (2.44 mol) of sodium hydroxide 50% aqueous solution were added while keeping at 20° to 40° C., heated and stirred for 30 minutes at 110° C. The solution was cooled to room temperature and 100 ml of toluene were added for separatory extraction. The toluene phase was washed with 100 ml of hydrochloric acid 5% aqueous solution and with 100 ml of water two times. The toluene solution obtained was dried by anhydrous sodium sulfate. 75.6 g (0.290 mol) of 1,2-bis(2-mercaptoethylthio)-3-mercaptopropane (formula (I) compound) were obtained as a colorless and viscous liquid (APHA 15) after concentration. Results of elemental analysis and NMR analysis are as follows:

| | Elemental analysis (as $C_7H_{16}S_5$) | | |
|---|---|---|---|
| | C | H | S |
| Found (%) | 32.12 | 6.19 | 61.69 |
| Calculated (%) | 32.27 | 6.19 | 61.53 |

$^1$H NMR analysis (in $CDCL_3$): $\delta_{PPM}$= 1.74–1.91 (m, 3H, —SH); 2.70–3.00 (m, 13H, CH)

$^{13}$C NMR (in $CDCl_3$)

$\delta_{ppm}$ =

24.7 —S—$CH_2CH_2$SH 24.9 —S—$CH_2CH_2$SH 28.6 —S—$CH_2CHCH_2$SH
         |
         S—

35.4 —S$CH_2CH_2$SH 36.0 —S$CH_2CH_2$SH 36.8 —S$CH_2CHCH_2$SH
         |
         S—

48.7 —S$CH_2CHCH_2$SH
         |
         S—

EXAMPLE 2

88.7 g (1.14 mol) 2-mercapto ethanol were added dropwise into 50.4 g (0.567 mol) of sodium hydroxide aqueous solution (45%) and homogenized. 50.5 g (0.546 mol) of epichlorohydrin were added dropwise to the homogenized solution extending over 1.5 hours, then kept at 112° C. for 0.5 hours with stirring.

After the reaction mixture cooled to room temperature, 270 g of concentrated hydrochloric acid (36%, 2.66 mol) and 154 g (2.02 mol) of thiourea were added to the mixture, and stirred for 1.5 hours at 112° C. 288 g of aqueous sodium hydroxide (45%, 3.24 mol) was added while keeping at 20° to 35° C. dropwise to the reaction mixture extending for 0.5 hours, and then stirred at 110° C. for 1.5 hours.

The reaction mixture was then cooled at room temperature, 200 ml of water and 250 ml of toluene were added for separatory extraction. The toluene phase was washed with 50 ml of hydrochloric acid (36%) and with 200 ml of water three times, then concentrated in vacuo and distilled (b.p 185°–205° C./0.4 Torr) and 105.8 g (0.406 mol) of 1,2-bis(2-mercaptoethylthio)-3-mercapto propane (Formula (I) compound) were obtained as a viscous liquid (APHA 10).

Results of elemental analysis and NMR analysis were same as of Example 1.

EXAMPLE 3

84.4 g (1.08 mol) of 2-mercapto ethanol were added to 0.8 g (0.001 mol) of 48.7% sodium hydroxide and homogenized, and then 50.0 g (0.540 mol) of epichlorohydrin was added to the solution dropwise below 40° C. extending over 0.5 hours, further kept the mixture stirring for 0.5 hours.

44.4 g (0.541 mol) of aqueous sodium hydroxide (48.7%) were added dropwise to the reaction mixture extending for 0.5 hours, and cooled with stirring to room temperature for 0.5 hours, 313 g (3.09 mol) of hydrochloric acid (36%) and 123.4 g (1.62 mol) of thiourea were added to the reaction mixture and stirred 1.5 hours at 112° C.

After cooling to room temperature, 254 g (3.09 mol) of aqueous sodium hydroxide (48.7%) was added to the reaction mixture at a range of temperature 25° to 35° C., then stirred and heated at 110° C. for 1.5 hours.

The reaction mixture was cooled to room temperature and 150 g of water and 180 g of toluene were added for separatory extraction. The toluene phase was washed with 150 g of hydrochloric acid (18%) and with 30 ml of water three times, then concentrated and distilled in vacuo (120° C./2 Torr, 2 hours) followed by a filtration with a filter (one micron pore size) to get 129 g (0.495 mol) of 1,2-bis(2-mercaptoethylthio)-3-mercaptopropane (formula (I) compound) as a viscous liquid (APHA 10).

Results of elemental analysis and NMR analysis were same as of Example 1.

EXAMPLE 4

84.4 g (1.08 mol) of 2-mercaptoethanol was added to 1.0 g (0.005 mol) of tributylamine, and 50.0 g (0.540 mol) of epichlorohydrin was added dropwise to the solution extending over 0.5 hours, and stirred further for 0.5 hours.

Then while cooling the mixture to a range of 40° to 70° C., 44.4 g (0.541 mol) of aqueous sodium hydroxide (48.7%) was added extending over 0.5 hours dropwise into the mixture.

After stirring for 0.5 hours, the mixture was cooled to room temperature and 313.1 g (3.09 mol) of hydrochloric acid (36%) and 123.4 g (1.62 mol) of thiourea, were added to the mixture then stirred for 1.5 hours at 112° C.

The reaction mixture was then cooled at room temperature, 254 g (3.09 mol) of aqueous sodium hydroxide (48.7%) was added while keeping at 25° to 35° C. and stirred at 110° C. for 1.5 hours.

Again after cooled the reaction mixture to room temperature, 150 ml of water and 180 ml of toluene were added for separatory extraction. The toluene phase was washed with 150 g of hydrochloric acid (18%) and with 30 g of water three times, then concentrated and distilled in vacuo (120° C./2 Torr, 2 hours), followed by a filtration with a filter (one micron pore size) to get 125 g (0.480 mol) of 1,2-bis(2-mercaptoethylthio)-3-mercaptopropane (formula (I) compound) as a viscous liquid (APHA 10)

Results of elemental and NMR analysis were same to as Example 1.

EXAMPLE 5

44.4 g (0.541 mol) of aqueous sodium hydroxide (48.7%) were added to a mixture of 84.4 g (1.08 mol) of 2-mercapto ethanol with 50.0 g (0.540 mol) epichlorohydrin, at a range between room temperature to 60° C. extending over one hour, further stirred the mixture at 80° for 0.5 hours.

After cooling to room temperature, 313 g (3.09 mol) of hydrochloric acid (36%) and 123.4 g (1.62 mol) of thiourea were added to the reaction mixture and stirred at 112° C. for 1.5 hours.

The reaction mixture was cooled again to room temperature, and 254 g (3.09 mol) of aqueous sodium hydroxide (48.7%) was added to the reaction mixture at a range of 25° C. to 35° C., and stirred at 110° C. for 1.5 hours.

After cooling to room temperature, 150 g of water and 180 g of toluene were added to the reaction mixture for separatory extraction. The toluene phase was washed with 150 g of hydrochloric acid (18%) and with 30 g of water three times, then concentrated and distilled in vacuo (120° C./2 Torr, 2 hours), filtered by a filter (pore size one micron) to get 122 g (0.468 mol) of 1,2-bis(2-mercaptoethylthio)-3-mercaptopropane (Formula (I) compound) as a viscous liquid (APHA 15), with the same elemental and NMR analysis data of Example 1.

EXAMPLE 6

735 g (1.50 mol) of sulfuric acid (20%) substituted for 270 g (2.66 mol) of hydrochloric acid (36%) in Example 2.

As a result, 102 g (0.392 mol) of 1,2-bis-(2-mercaptoethylthio)-3-mercaptopropane (Formula (I) compound) with the same data on elemental and NMR analysis of Example 1.

EXAMPLE 7

327 g (1.00 mol) of phosphoric acid (30%) substituted for 270 g (2.66 mol) of hydrochloric acid (36%) in Example 2.

100 g (0.384 mol) of 1,2-bis-(2-mercaptoethylthio)-3-mercaptopropane (Formula (I) compound) resulted with the same data on elemental and NMR analysis of Example 1.

EXAMPLE 8

53.2 g (0.681 mol) of 2-mercaptoethanol and 27.2 g (0.680 mol) of sodium hydroxide were dissolved into 200 ml of ethanol and homogenized, 70.0 g (0.324 mol) of 2,3-dibromo-1-propanol were added dropwise to the ethanol solution while keeping an inner temperature of 15° C.

The mixture was heated to 50° C. and stirred for one hour, followed by a cooling to room temperature to form a precipitate. The salt precipitated was separated by filtration with suction. The filtrate was concentrated under reduced pressure and 71.3 g of a mixture of 1,3-bis(2-hydroxyethylthio)-2-propanol (Formula (II) compound) with 1,2-bis(2-hydroxyethylthio)-3-propanol (Formula (III) compound) as a colorless and viscous liquid.

The mixture was dissolved in 203 g (2.00 mol) of hydrochloric acid (36%) and 92.6 g (1.22 mol) of thiourea were added to the solution. The solution was cooled to room temperature, and 195 g (2.44 mol) of sodium hydroxide 50% aqueous solution were added while keeping at 20° to 40° C., heated and stirred for 30 minutes at 110° C.

The solution was cooled to room temperature and 100 ml of toluene were added for separatory extraction. The toluene phase was washed with 100 ml of hydrochloric acid 5% aqueous solution and with 100 ml of water two times. The toluene solution obtained was dried by anhydrous sodium sulfate. 75.6 g (0.290 mol) of 1,2-bis(2-mercaptoethylthio)-3-mercaptopropane (Formula (I) compound) were obtained as a colorless and viscous liquid (APHA 15) after concentration.

Results of elemental analysis and NMR analysis are as follows:

| Elemental analysis (as $C_7H_{16}S_5$) | | | |
|---|---|---|---|
| | C | H | S |
| Found (%) | 32.14 | 6.17 | 61.69 |
| Calculated (%) | 32.27 | 6.19 | 61.53 |

$^1$H NMR analysis (in CDCl$_3$): $\delta_{ppm}$=1.74–1.91 (m, 3H, —S$\underline{H}$); 2.70–3.00 (m, 13H, C$\underline{H}$)

$^{13}$C NMR (in CDCl$_3$)

$\delta_{ppm}$ =

24.7 —SCH$_2$$\underline{C}$H$_2$SH 24.9 —SCH$_2$$\underline{C}$H$_2$SH 28.6 —SCH$_2$CH$\underline{C}$H$_2$SH
　　　　　|
　　　　　S—

35.4 —S$\underline{C}$H$_2$CH$_2$SH 36.0 —S$\underline{C}$H$_2$CH$_2$SH 36.8 —S$\underline{C}$H$_2$CHCH$_2$SH
　　　　　|
　　　　　S—

48.7 —SCH$_2$$\underline{C}$HCH$_2$SH
　　　　　|
　　　　　S—

EXAMPLE 9

A mixture of 87 g of the compound obtained in Example 1 and 94 g of m-xylylene diisocyanate were homogenized and were poured into a mold composed of a glass mold and gasket, and then were heated and cured. The resin produced was colorless and transparent, excellent in high impact resistance, had a refractive index $n_D20$ of 1.66 and Abbe's number $\nu_D$ of 33 and a heat distortion starting temperature of 98° C.

EXAMPLES 10–28 AND COMPARATIVE EXAMPLES 1 TO 11

Following the procedure of Example 9, lenses were prepared in composition ratios shown in Table 1. The results of performance tests are set forth in Table 1.

| | Ester Compound (Polyisothiocyanate, amount by mole) | Polythiol | | Refractive index | Abbe's Number | Weather-ability | Appearance | Odor | Heat resistance (°C.) |
|---|---|---|---|---|---|---|---|---|---|
| Example 9 | m-Xylylenediisocyanate | (0.5) 1,2-Bis-(2-mercaptoethylthio)-3-mercaptopropane (Compound of formula (I)) | (0.33) | 1.66 | 33 | ○ | Colorless and transparent | ○ | 98 |
| Example 10 | Isophoronediisocyanate | (0.5) 1,2-Bis-(2-mercaptoethylthio)-3-mercaptopropane (Compound of formula (I)) | (0.33) | 1.60 | 40 | ○ | Colorless and transparent | ○ | 142 |
| Example 11 | 1,4-bis(isocyanate methyl) cyclohexane | (0.5) 1,2-Bis-(2-mercaptoethylthio)-3-mercaptopropane (Compound of formula (I)) | (0.33) | 1.62 | 39 | ○ | Colorless and transparent | ○ | |
| Example 12 | OCN—(CH₂)₆—NCO | (0.5) 1,2-Bis-(2-mercaptoethylthio)-3-mercaptopropane (Compound of formula (I)) | (0.33) | 1.62 | 39 | ○ | Colorless and transparent | ○ | |
| Example 13 | m-Xylylenediisocyanate Tolylenediisocyanate | (0.4) (0.1) 1,2-Bis-(2-mercaptoethylthio)-3-mercaptopropane (Compound of formula (I)) | (0.33) | 1.67 | 30 | ○ | Colorless and transparent | ○ | |
| Example 14 | Thiodiethyldiisocyanate | (0.5) 1,2-Bis-(2-mercaptoethylthio)-3-mercaptopropane (Compound of formula (I)) | (0.33) | 1.65 | 34 | ○ | Colorless and transparent | ○ | |
| Example 15 | Dithiodiethyldiisocyanate | (0.5) 1,2-Bis-(2-mercaptoethylthio)-3-mercaptopropane (Compound of formula (I)) | (0.33) | 1.67 | 33 | ○ | Colorless and transparent | ○ | |
| Example 16 | Dithiodipropyldiisocyanate | (0.5) 1,2-Bis-(2-mercaptoethylthio)-3-mercaptopropane (Compound of formula (I)) | (0.33) | 1.65 | 34 | ○ | Colorless and transparent | ○ | |
| Comparative example 1 | m-Xylylenediisocyanate | (0.25) Pentaerythritol-tetrakis(3-mercaptopropionate) | (0.25) | 1.59 | 36 | ○ | Colorless and transparent | × | 84 |
| Comparative example 2 | m-Xylylenediisocyanate | (0.5) Tetrabrombisphenol A | (0.5) | 1.61 | 27 | △ | Transparent slightly yellowish | ○ | |
| Comparative example 3 | Hexamethylenediisocyanate | (0.5) 1,4-Butanediol | (0.5) | 1.50 | 55 | ○ | Transparent Colorless | ○ | |
| Comparative example 4 | Isophoronediisocyanate | (0.5) Pentaerythritoltetrakis-(3-mercaptopropionate) | (0.25) | 1.54 | 47 | ○ | Transparent Colorless | × | 117 |
| Example 17 | SCN⟨CH₂⟩₆NCS | (0.5) 1,2-Bis-(2-mercaptoethylthio)-3-mercaptopropane (Compound of formula (I)) | (0.33) | 1.70 | | ○ | Transparent Colorless | ○ | |
| Example 18 | SCN—⟨phenyl⟩—S—S—⟨phenyl⟩—NCS | (0.5) 1,2-Bis-(2-mercaptoethylthio)-3-mercaptopropane (Compound of formula (I)) | (0.33) | 1.77 | | ○ | Transparent Colorless | ○ | |
| Example 19 | S(CH₂CH₂NCS)₂ | (0.5) 1,2-Bis-(2-mercaptoethylthio)-3-mercaptopropane (Compound of formula (I)) | (0.33) | 1.73 | | ○ | Transparent Colorless | ○ | |

TABLE 1-continued

| Example | Ester Compound (Polyisothiocyanate, amount by mole) | Polythiol | (mole) | Refractive index | Abbe's Number | Weather-ability | Appearance | Odor | Heat resistance (°C.) |
|---|---|---|---|---|---|---|---|---|---|
| Example 20 | SCN—C₆H₄—NCS | 1,2-Bis-(2-mercaptoethylthio)-3-mercaptopropane (Compound of formula (II)) | (0.5) (0.33) | 1.75 | | ○ | Transparent Colorless | ○ | |
| Comparative Example 5 | m-Xylylenediisocyanate | Pentaerythritoltetrakis-(thioglycolate) | (0.5) (0.33) | 1.60 | 34 | ○ | Transparent Colorless | x | |
| Comparative Example 6 | m-Xylylenediisocyanate | Ethanedithiol | (0.5) (0.5) | 1.65 | | ○ | Transparent Colorless | x | |
| Comparative Example 7 | m-Xylylenediisocyanate | Xylylenedithiol | (0.5) (0.5) | 1.66 | 29 | ○ | Transparent Colorless | x | |
| Comparative Example 8 | m-Xylylenediisocyanate | 1,3-Propanedithiol | (0.5) (0.5) | 1.64 | | ○ | Transparent Colorless | x | |
| Example 21 | OCN(CH₂)₆NCS | 1,2-Bis-(2-mercaptoethylthio)-3-mercaptopropane (Compound of formula (II)) | (0.33) (0.33) | 1.67 | | ○ | Transparent Colorless | ⊙ | |
| Example 22 | OCN—C₆H₄—NCS | 1,2-Bis-(2-mercaptoethylthio)-3-mercaptopropane (Compound of formula (II)) | (0.5) (0.33) | 1.72 | | ○ | Transparent Colorless | ○ | |
| Example 23 | OCN—C₆H₁₀—NCS | 1,2-Bis-(2-mercaptoethylthio)-3-mercaptopropane (Compound of formula (II)) | (0.5) (0.33) | 1.68 | | ○ | Transparent Colorless | ○ | |
| Example 24 | OCN—C₆H₄—S—C₆H₄—NCS | 1,2-Bis-(2-mercaptoethylthio)-3-mercaptopropane (Compound of formula (II)) | (0.5) (0.33) | 1.74 | | ○ | Transparent Colorless | ○ | |
| Example 25 | S(CH₂CH₂NCO)(CH₂CH₂NCS) | 1,2-Bis-(2-mercaptoethylthio)-3-mercaptopropane (Compound of formula (II)) | (0.5) (0.33) | 1.70 | | ○ | Transparent Colorless | ○ | |
| Example 26 | S—CH₂CH₂NCO / S—CH₂CH₂NCS | 1,2-Bis-(2-mercaptoethylthio)-3-mercaptopropane (Compound of formula (II)) | (0.5) (0.33) | 1.71 | | ○ | Transparent Colorless | ○ | |
| Comparative example 9 | S—CH₂CH₂NCO / S—CH₂CH₂NCS | C(CH₂SCH₂CH₂SH)₄ | (0.5) (0.25) | 1.71 | | ○ | Transparent Colorless | x | |

TABLE 1-continued

| | Ester Compound (Polyisothiocyanate, amount by mole) | | Polythiol | (mole) | Refractive index | Abbe's Number | Weather-ability | Appearance | Odor | Heat resistance (°C.) |
|---|---|---|---|---|---|---|---|---|---|---|
| Comparative Example 10 | S—CH₂CH₂NCO<br>S—CH₂CH₂NCS | (0.5) | CH₂SH / CH₂SH (m-xylylene) | (0.5) | 1.71 | — | ○ | Transparent Colorless | X | — |
| Example 27 | 2,4-diisocyanato toluene (NCO, NCO, CH₃) | | 1,2-Bis-(2-mercaptoethylthio)-3-mercaptopropane (Compound of formula (I)) | (0.33) | 1.69 | 26 | ○ | Transparent Colorless | ○ | 140 |
| Example 28 | norbornane diisocyanate (CH₂NCO / OCNCH₂) | | 1,2-Bis-(2-mercaptoethylthio)-3-mercaptopropane (Compound of formula (I)) | (0.33) | 1.62 | 41 | ○ | Transparent Colorless | ○ | 118 |
| Comparative Example 11 | 2,4-diisocyanato toluene (NCO, NCO, CH₃) | | Pentaerythritoltetrakis-(3-mercaptopropionate) | (0.25) | 1.62 | 32 | X | Pale yellowish transparent | X | 125 |

What is claimed is:

1. A polythiourethane base resin comprising reacting a mercapto compound of the formula (I)

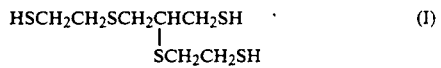

with at least one ester compound selected from the group consisting of polyisocyanate compounds, polyisothiocyanate compounds and isothiocyanate compounds having a isocyanato groups.

2. The resin of claim 1 wherein the mole ratio of said at least one ester compound to said mercapto compound is from about 0.5 to about 3.0 moles of functional (NCO+NCS) groups per mole of functional mercapto group.

3. The process for preparing the resin of claim 1 wherein the reaction is carried out by heating and curing.

4. The process for preparing the resin of claim 2 wherein the reaction is carried out by heating and curing.

5. A plastic lens comprising reacting a mercapto compound of the formula (I)

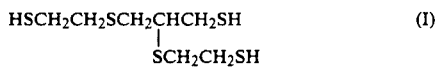

with at least one ester compound selected from the group consisting of polyisocyanate compounds, polyisothiocyanate compounds and isothiocyanate compounds having a isocyanato groups.

6. The lens of claim 5 wherein the mole ratio of said at least one ester compound to said mercapto compound is from about 0.5 to about 3.0 moles of functional (NCO+NCS) groups per mole of functional mercapto group.

7. A process for producing a plastic lens comprising mixing a mercapto compound of the formula (I)

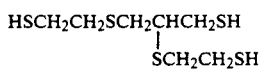

with at least one ester compound selected from the group consisting of polyisocyanate compounds, polyisothiocyanate compounds and isothiocyanate compounds having a isocyanato groups to form a mixture; casting and polymerizing the mixture to form a plastic lens.

8. The process of claim 7 wherein the mole ratio of said at least one ester compound to said mercapto compound is from about 0.5 to about 3.0 moles of functional (NCO+NCS) groups per mole of functional mercapto group.

9. The process of claim 7 comprising adding to said mixture at least one compound selected from the group consisting of internal mold release agents, chain extenders, crosslinking agents, light stabilizers, ultraviolet absorbers, anti-oxidants, oil-soluble dyes and fillers.

* * * * *